Dec. 18, 1962 M. L. WHISLER Plant Pat. 2,203
ROSE PLANT
Filed Feb. 19, 1962
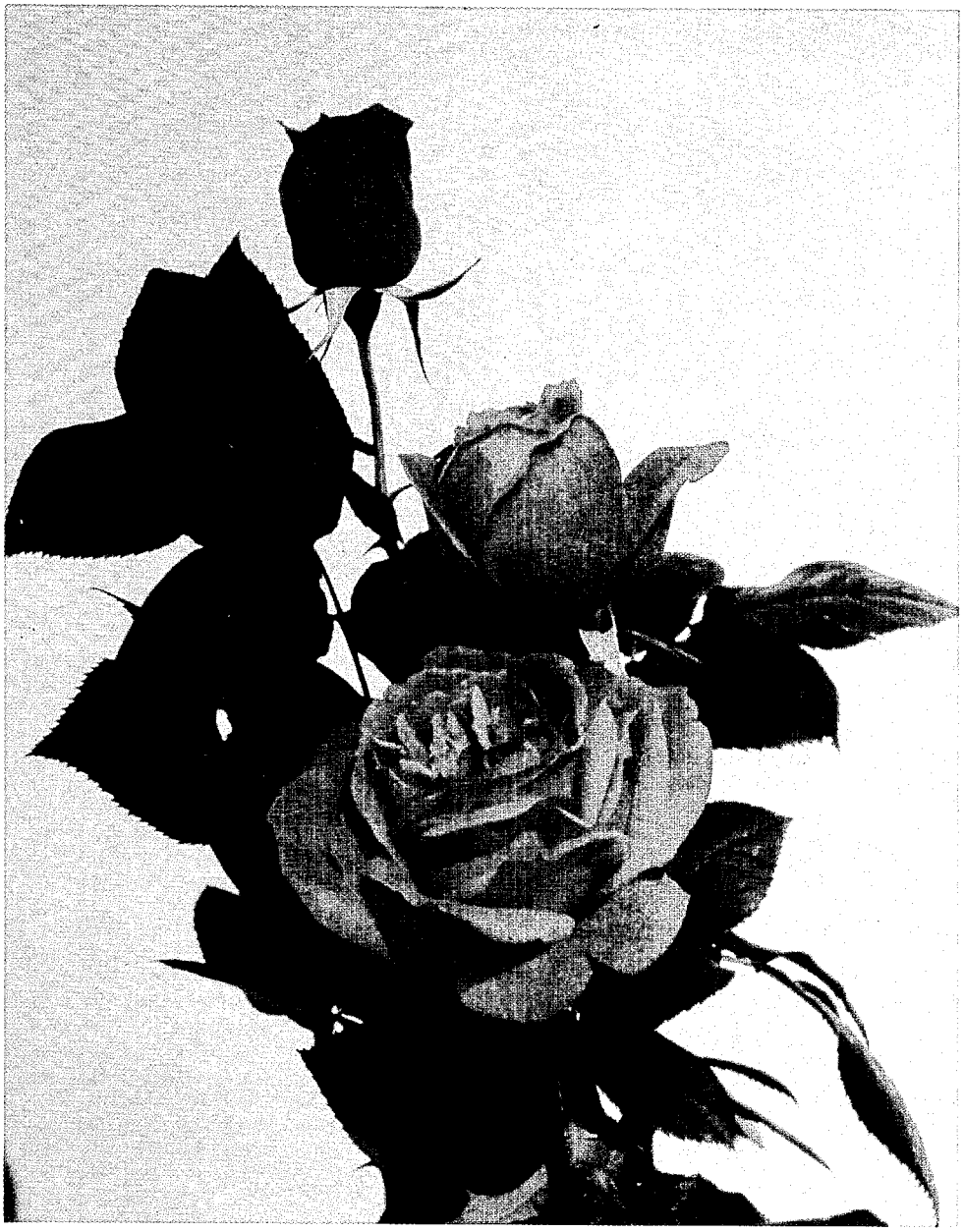
Inventor.
Milton L. Whisler
By: Robb & Robb
Attorneys.

United States Patent Office

Plant Pat. 2,203
Patented Dec. 18, 1962

2,203
ROSE PLANT

Milton L. Whisler, Shafter, Calif., assignor to Germain's, Inc., Los Angeles, Calif., a corporation of California Filed Feb. 19, 1962, Ser. No. 174,326
1 Claim. (Cl. 47—61)

The present invention relates to a new and distinct variety of rose plant of the hybrid tea class, which was originated by me by crossing the variety known as "Chrysler Imperial" (Plant Patent No. 1,167) with an unnamed and unpatented seedling of unidentified parentage.

As the result of this breeding, I have succeeded in producing a new rose variety having a unique combination of characteristics which are especially desirable and which distinguish the new variety from its parents, as well as from all other varieties of which I am aware. The following characteristics are the most outstanding in this new combination:

(1) An upright, bushy and moderately vigorous habit of plant growth;

(2) Quite heavy foliage of medium large size and leathery texture;

(3) Closely spaced leaf nodes on the stems, canes and branches, which result in giving the plant a well-clothed appearance;

(4) Very heavy petal substance, with consequent exceptional long lasting quality of the blooms both on the plant and as cut flowers; and (5) A distinctive and attractive clear orange-red general color tonality of the flowers, accompanied by exceptionally good finishing reaction without exhibiting the usual symptoms of petal burning or degeneration of the red and orange colorations.

Asexual reproduction of my new variety by budding, as performed at Saugus, California, shows that the foregoing characterics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with colour terminology in accordance with the Horticultural Colour Chart of the British Colour Council, except where general color terms of ordinary dictionary significance are obvious:

Type: Half-hardy; bush; outdoor; seedling; for cut flowers and for garden decoration.
Class: Hybrid tea.
Breeding: Seedling.
*Seed parent.*—"Chrysler Imperial."
*Pollen parent.*—An unnamed seedling of unidentified parentage.
Propagation: Holds its distinguishing characteristics through succeeding propagations by budding.

*Flower*

Locality where grown and observed: Shafter, California.
Flowers borne: Both singly and several to stem; on stems of medium length and normal strength.
Quantity of bloom: Abundant, outdoors.
Continuity: Continuous.
Fragrance: Moderate.
*Nature.*—Tea.
Bud:
*Peduncle.*—Medium length; medium heaviness; medium erectness; almost smooth; with numerous red-brown prickles. Color—green.

*Before calyx breaks.*—Size—medium. Form—oval; without foliaceous appendages on the surface of the bud; without foliaceous parts extending beyond the tip of the bud. Color—Blood Red, Plate 820/1.
*As calyx breaks.*—Color—Blood Red, Plate 820/1.
*As first petals open.*—Size—medium. Form—globular. Color—outside—Orient Red, Plate 819/2; inside—Orient Red, Plate 819, shading to Geranium Lake, Plate 20.
*Opening.*—Opens up well; opening is retarded by cold weather.
Bloom:
*Size (when fully open).*—Medium; from 4 inches to 5 inches.
*Petalage.*—Very double; from 35 to 40 petals; arranged regularly.
*Form.*—Full and globular at first but becoming open and high-centered; petals being at first loosely rolled outward, and remaining loosely rolled outward at maturity.
Petals:
*Texture.*—Thick; leathery.
*Appearance.*—Inside—velvety. Outside—satiny.
*Shape.*—Outside—oval, with one notch. Intermediate—ovate; scalloped; with apex flat and with one notch. Inside—obovate; irregularly scalloped.

This description of a newly opened flower was made from a rose grown outdoors during the month of October at Shafter, California.

*Color.*—Outer petal—Outside surface—Blood Red, Plate 820; inside surface—Scarlet, Plate 19. Intermediate petal — outside surface — Geranium Lake, Plate 20/1; inside surface—Geranium Lake, Plate 20. Inner petal—outside surface—Blood Red, Plate 820/3; inside surface—Scarlet, Plate 19.

This description was made from a rose that was open for three days outdoors during the month of October at Shafter, California:

*Color.*—Outer petal—outside surface—Blood Red, Plate 820; inside surface—Geranium Lake, Plate 20/1. Inner petal—outside surface—Claret Rose, Plate 021/1; inside surface—Geranium Lake, Plate 20/2.
*General color effect.*—Newly opened flower—Geranium Lake, Plate 20. Three days open—Geranium Lake, Plate 20/1.
*Behavior.*—Persist; fading from Turkey Red, Plate 721, to Carmine, Plate 21/1.
*Flower longevity.*—On bush in garden—5 days in September. Cut flowers grown outdoors and kept at living room temperatures—5 days in September.

*Reproductive organs*

Stamens: Many; regularly arranged about pistils.
*Color.*—Indian Yellow, Plate 6.
Filaments: Medium length; with anthers.
*Color.*—Reddish.
Anthers: Medium size; open at various times.
*Color.*—Yellow.
Pollen: Moderate abundance.
*Color.*—Gold.
Pistils: Many.
Styles: Uneven; medium length; bunched.
Stigma:
*Color.*—Yellow.
Ovaries: All enclosed in calyx.

Hips: Pear-shaped; very smooth; walls thick and fleshy.
*Color.*—From yellow to reddish.
Sepals: Permanent.
*Color.*—Bronze-Green.
Seeds: Few; medium size.

*Plant*

Foliage:
*Leaves.*—Compound of 5 leaflets; abundant; medium large size; moderately heavy; leathery.
*Leaflets.*—Shape—ovoid. Base—round. Margin—simply serrate.
*Color.*—Mature—upper surface—dark green; under surface—light green. Young—upper surface—very bronze; under surface—red.
*Rachis (the supporting stem of the compound leaf).*—Medium. Upper side—smooth. Under side—sparsely prickly.
*Stipules.*—Medium length; moderately narrow; with medium long points turning out at an angle of less than 45°.
*Disease resistance.*—More resistant to mildew than parent varieties and no blackspot, as determined by comparison with other varieties grown under comparable cultural conditions at Shafter, California.
Growth:
*Habit.*—Bushy; upright.
*Growth.*—Moderately vigorous.
*Canes.*—Medium caliper.

*Main stems.*—Color—dull bronze. Thorns—many; straight; with long, narrow base. Prickles—few; color—brown. Hairs—few; color—bronze.
*Branches.* — Color—dull green-bronze. Thorns—many; medium length; straight; with long, narrow base. Prickles—few; color—reddish. Hairs—none.
*New shoots.*—Color—bright bronze-red. Thorns—many; medium length; straight; with long, narrow base. Prickles—few; color—reddish. Hairs—none.

I claim:

A new and distinct variety of rose plant of the hybrid tea class, substantially as herein shown and described, characterized particularly as to novelty by the unique combination of an upright, bushy and moderately vigorous habit of plant growth, quite heavy foliage of medium large size and leathery texture, closely spaced leaf nodes on the stems, canes and branches which give the plant a well-clothed appearance, very heavy petal substance and consequent long-lasting quality of the blooms both on the plant and as cut flowers, and a distinctive and attractive clear orange-red general color tonality of the flowers accompanied by an exceptionally good finishing reaction without exhibiting the usual symptoms of petal burning or degeneration of the red and orange colorations.

No references cited.